United States Patent [19]

Marinberg et al.

[11] Patent Number: 5,060,324
[45] Date of Patent: Oct. 29, 1991

[54] INFLATABLE APPARATUS FOR IMMOBILIZING AND CHANGING POSITIONS OF A PATIENT

[76] Inventors: Boris V. Marinberg, 711 Appletree La., Glencoe, Ill. 60022; Leah W. Ratner, 820 W. Belle Plaine #804, Chicago, Ill. 60613

[21] Appl. No.: 556,352

[22] Filed: Jul. 23, 1990

[51] Int. Cl.$^5$ .................. A61G 7/08; A47C 27/08
[52] U.S. Cl. .................. 5/81 R; 5/82 R; 5/431; 5/457; 128/873
[58] Field of Search .............. 5/81 R, 81 B, 82 R, 5/61, 449, 455, 431, 457; 128/869, 870, 873, 874; 2/DIG. 3

[56] References Cited

U.S. PATENT DOCUMENTS

| | | | |
|---|---|---|---|
| 1,981,666 | 11/1934 | Ridley | 5/81 R |
| 3,462,775 | 8/1969 | Markwitz | 5/449 |
| 3,811,433 | 5/1974 | Brachet | 5/82 |
| 3,914,811 | 10/1975 | Francis | 5/455 |
| 4,301,791 | 11/1981 | Franco | 5/455 |
| 4,428,087 | 1/1984 | Horn | 5/455 |
| 4,466,145 | 8/1984 | Jones | 5/82 R |
| 4,607,655 | 8/1986 | Wagner | 5/82 R |
| 4,872,226 | 10/1989 | Lonardo | 5/81 R |
| 4,885,811 | 12/1989 | Hayes | 5/82 R |

Primary Examiner—Michael F. Trettel
Assistant Examiner—F. Saether
Attorney, Agent, or Firm—I. Michael Bak-Boychuk

[57] ABSTRACT

A substantially rectangular confining envelope characterized by an exterior and interior polymeric skin bonded to each other in bonding seams which include gaps for conveying air to the adjacent sections. The longitudinal edges of the envelope may include fastening devices for engagement of the envelope around the body of a patient. One or more of the gaps may then be selectively closed to control the distribution of compressed air in the envelope.

2 Claims, 2 Drawing Sheets

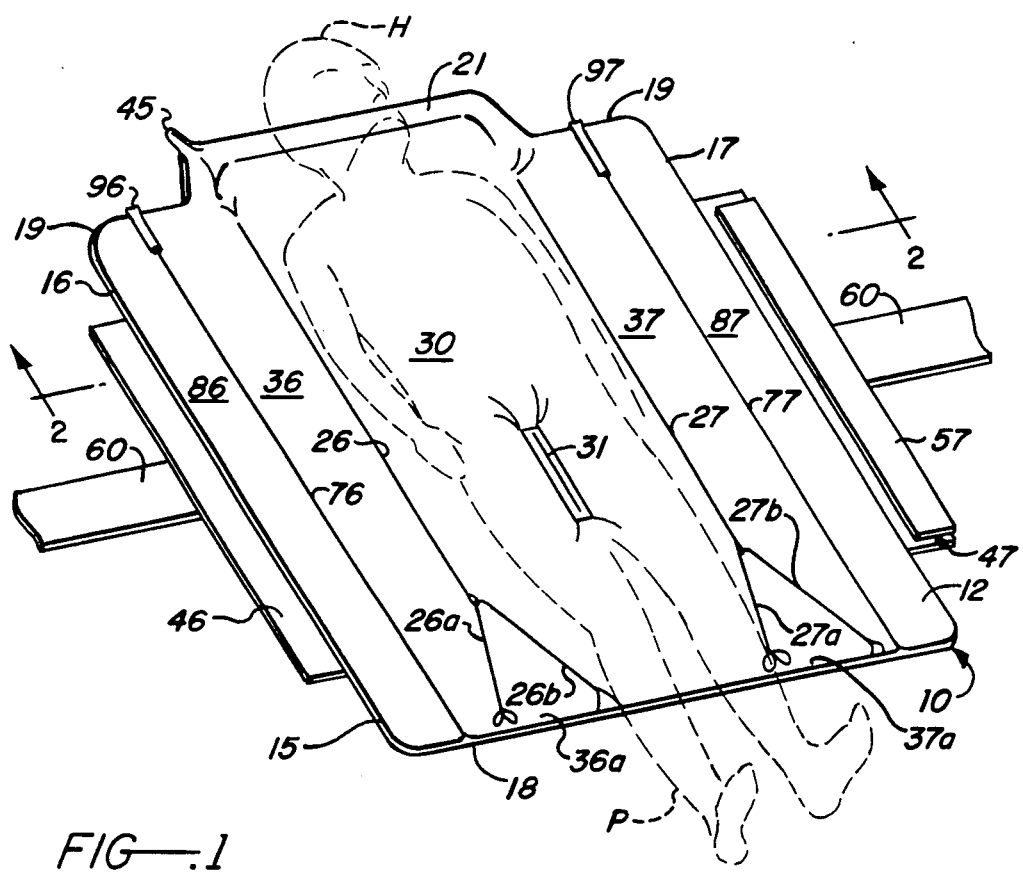
FIG—.1
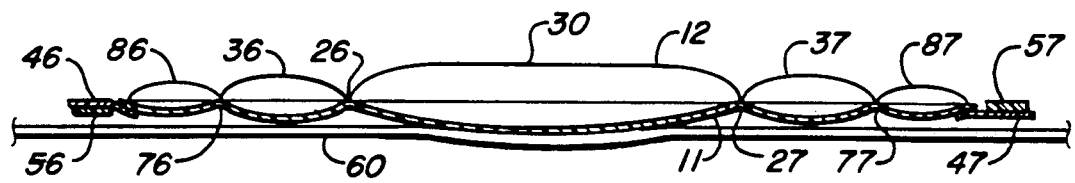
FIG—.2

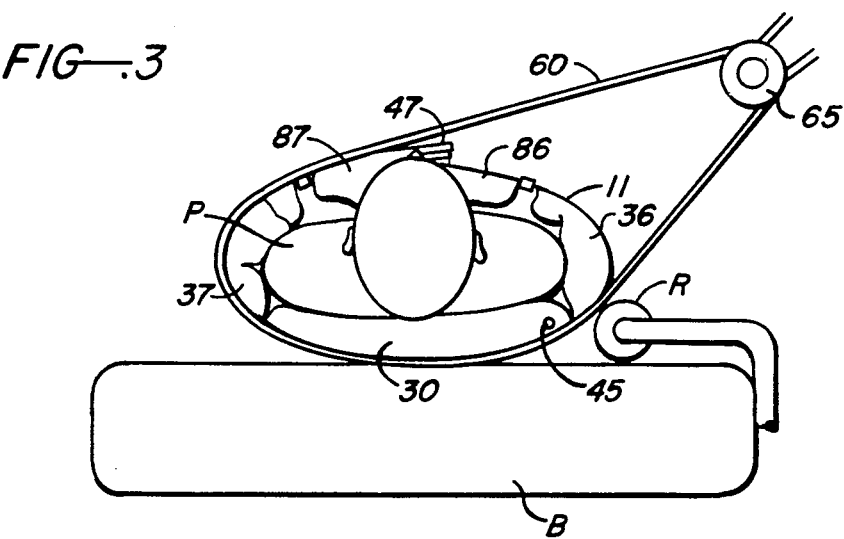
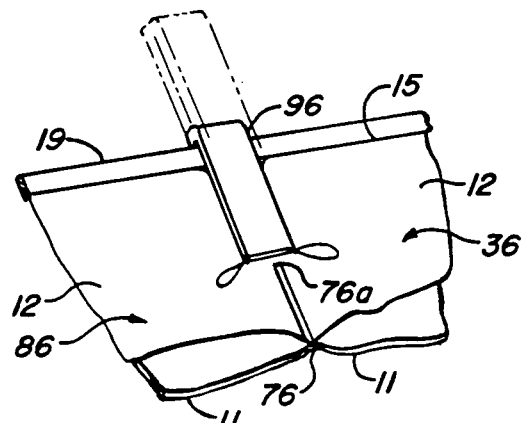
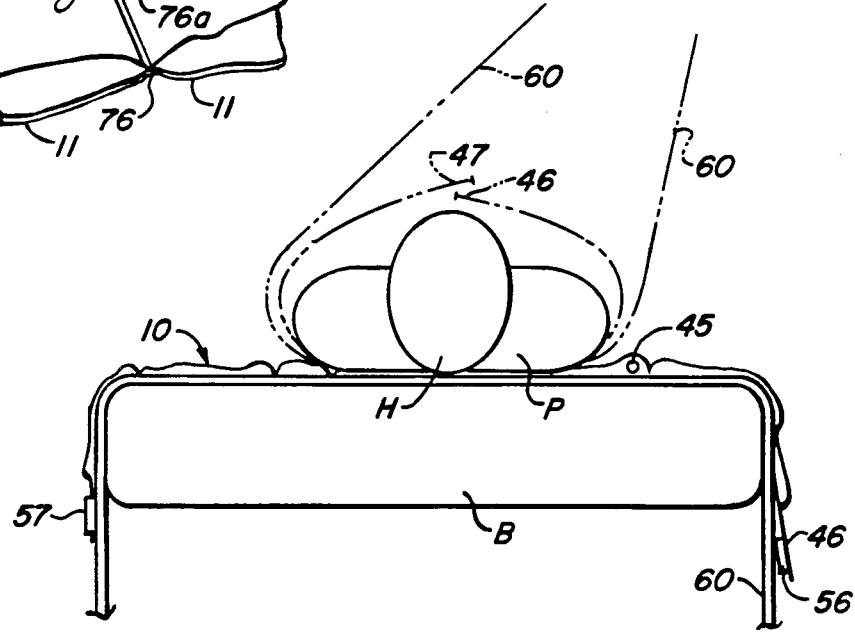

INFLATABLE APPARATUS FOR IMMOBILIZING AND CHANGING POSITIONS OF A PATIENT

BACKGROUND OF THE INVENTION

1. Field of the Invention

The present invention relates to inflatable structures for immobilizing a patient and, more particularly, to whole body inflatable envelopes which restrain the person of a patient and which facilitate positioning of patients stricken with loss of muscular control.

2. Description of the Prior Art

The use of inflatable devices to restrain or support the limbs of a person has been known in the past. In preferred practice such a device, once inflated, provides the function of a splint or a retainer which confines and fixes the injured limb from further motion. Prior or subsequent to inflation the device is folded and stored.

Thus, the use and advantages of inflated enclosures for restraining injured limbs has been known in the past and the benign aspects of even pressure distribution are widely appreciated.

In many instances, however, the physical state of a patient involves an impairment of the whole body. Thus, those suffering from stroke, spinal cord injury and other injury to the motor facilities of the musculature often require restraints and physical assistance in positioning or alignment. The assistance necessary for patient positioning during therapeutic and diagnostic events is often quite involved and the presence of assistants during X-ray and other procedures is an event of some frequency.

Concurrently, these same bedridden patients require constant attention in their repose. The loss of all muscular facility results in the necessity of limb and body restraints and constant attention to torso alignment both to relieve pressure points and to accommodate proper body functioning.

In the past various devices have been provided which, in one manner or another, restrain or aid in positioning of a patient. Exemplary teachings of such devices are found in U.S. Pat. Nos. 3,783,863 and 3,775,781. Each of these teachings, while suitable for the purposes intended, fails to provide for convenient manipulation and positioning of the patient in the course of therapeutic or diagnostic movement.

A convenient inflatable enclosure is therefore desired and it is one such enclosure that is disclosed herein.

SUMMARY OF THE INVENTION

Accordingly, it is the general purpose and object of the present invention to provide an air inflatable patient enclosure which is useful both to restrain the patient and to position the patient by turning.

Other objects of the invention are to provide an air inflatable patient enclosure segmented for even pressure distribution.

Yet further objects of the invention are to provide an air inflatable restraining enclosure for immobilizing the body of a patient.

Briefly, these and other objects are accomplished within the present invention by providing a substantially rectangular envelope defined by an outer, air impervious, polymeric skin and an inner air impervious polymeric skin joined to each other at their peripheries. The outer and inner skins, moreover, may be bonded to each other along selected fold lines for controlling the inflated shape of the envelope and for defining the points at which folding takes place. A valve in the outer skin is then useful in admitting air into the envelope.

Preferably, the envelope is divided by the fold line bonds into five commonly manifolded longitudinal panels, the center panel being generally of the width of the torso and the side panels being of sufficient width to overlap at the edges when folded over the person. The outer panels, at each edge, are provided with selective manifold controls and therefore may be isolated in inflation. This selective manifolding provides the necessary envelope control for the various body shapes contained.

To effect selective closure the lateral edges of the envelope are respectively provided with edge flaps each including an overlapping hook and pile strip generally known by the trademark, "Velcro" or any other closure device such as a zipper or buckle straps. Thus, the envelope may be conveniently fitted to surround the torso of the patient.

Once thus fitted the envelope is then inflated to an internal pressure sufficient to support the patient. Preferably the outer skin is formed of a substantially thicker section as that of the inner skin. Thus, the lateral dimension of the outer skin is generally fixed and, in consequence, the hoop dimension of closed overlapping envelope is generally fixed. In consequence, the envelope expands to a generally tubular form upon inflation with the irregular shape of the patient conformed by the folds of the inner skin.

A transverse strap of some width is fixed at its center point to a central area of the outer skin. The ends of the strap are then passed over and under the overlapped envelope to join in a common slip fitting, the extent of engagement of each end in the fitting determining the turning moments applied. While thus turned the patient confined in the envelope is kept within the limits of the bed frame by one or more lateral rollers opposing further rolling migration.

In this manner the patient may be conveniently positioned for various diagnostic procedures in an envelope which also serves as a bed positioner.

BRIEF DESCRIPTION OF THE DRAWINGS

FIG. 1 is a perspective illustration of the inventive patient restraining envelope in its unfolded form;

FIG. 2 is a sectional view, taken along line 2-2 of FIG. 1 of the inventive envelope in its released form;

FIG. 3 is a sectional view of the inventive envelope in its restraining engagement;

FIG. 4 is a diagrammatic illustration of a folding sequence of the inventive envelope; and FIG. 5 is a perspective detail of a typical manifold closure useful in selectively controlling the inflation of portions of the inventive envelope.

DESCRIPTION OF THE PREFERRED EMBODIMENT

As shown in FIGS. 1-4 the inventive envelope, generally designated by the numeral 10, is characterised by an outer and inner air impervious skin, 11 and 12, respectively, each of a generally rectangular plan form and bonded to each other by way of a peripheral bonding seam 15. In this form skins 11 and 12 combine to form a substantially rectangular cavity defined by lateral edges 16 and 17 and a lower edge 18. At the upper edge 19 the cavity expands into a central extension 21 to support the neck and a part of the head H of the patient P.

To provide for controlled geometry and fold locations the inner and outer skins 12 and 11 are bonded to each other along four longitudinal bond seams 26, 27, 76 and 77, which thus separate the envelope into a center panel 30 between two lateral panels 36 and 37 at either side thereof and two edge panels 86 and 87 at the distal sides of panels 36 and 37. Bond seams 26, 27, 76 and 77 extend to less than the full length of the envelope. Thus, a manifolded air passage is provided across each bond seam for inflation. This air passage into panels 86 and 87 may be selectively closed by closure clips 96 and 97 at each gap in seams 76 and 77. In consequence the edge panels 86 and 87 are either inflated or left uninflated following closure. This, then, controls the sectional expanded shape of the closed envelope to accommodate patients of various body sizes.

To accommodate access for bodily functions, and to give access for catheters, enemas, and the like, panel 30 may include an aperture 31 subjacent the torso. Thus, as the patient is immobilized full access for all necessities is provided.

Preferably the longitudinal dimension of panels 30, 36 and 37 extends for the full torso length of the patient P and partly onto the legs. To provide lateral leg confinement the lower ends of seams 26 and 27 are branched into forked seam pairs 26a, 26b, 27a and 27b. These then define triangular panels 36a and 37a.

In use the patient P is positioned onto the center panel 30 with the head H located on extension 21. Panel 86 is then wrapped over the patient and then overlaid by panel 87. To effect a surrounding closure the edges 16 and 17 are provided with longitudinal closure tabs 46 and 47, tab 46 being bonded on the exterior to a hook and pile strip 56 while tab 47 includes a similar mating strip 57 on the interior. It is these strips that effect a surrounding closure around a patient. Of course, various other closure mechanisms may be provided (not shown).

Once the closure is thus effected air is admitted across a valve 45 in the exterior skin 11. Preferably skin 12 is substantially thicker than skin 11 and is thus dimensionally less compliant than the inner skin. Consequently, the outer skin 11 serves to retain in hoop the pneumatic expansion of the envelope. This then results in a substantially tubular exterior shape of the closed envelope. A strap 60 is then useful in turning the patient, strap 60 being fixed to the exterior of the center panel 30 to pass the the ends thereof around the envelope.

The ends of strap 60 may be received in a common slip fitting 65. The dimensional receipt of the ends of the strap in the fitting then determines the rolling moment applied to the envelope. Manual force to the slip fitting 65, or to either end of the strap, is then effective to move or trun the patient on the bed surface B. A roller R at the edge of the bed may provide a rolling barrier to assist in turning.

By reference to FIG. 5 one will note that the bonding seam 76 (and by the same example seam 77) terminates at its upper end in a bond end 76a, thus leaving an unbonded segment adjacent the edge 19. Clip 96 (and similarly clip 97) is generally U-shaped and thus may be inserted onto the skins 11 and 12 to span this unbonded segment. Thus, clips 96 and 97 are useful in closing the air passage to panels 86 and 87 at any selected level of inflation. This then provides the desired control over the final inflated shape, including lower inflation levels in the panels confining the patient's chest and hands.

Obviously many modifications and changes may be made to the foregoing description without departing from the spirit of the invention. It is therefore intended that the scope of the invention be determined solely on the claims appended hereto.

What is claimed is:

1. An inflatable envelope for enclosing the body of a patient, comprising:
   an exterior resilient membrane of substantially rectangular planform extending substantially the entire length of the body of the patient;
   an interior resilient membrane of a planform substantially equal to said rectangular planform of said exterior membrane, said interior membrane being joined at the periphery thereof to the periphery of said exterior membrane to form an air impervious containment structure in combination therewith, said exterior membrane including valve means for admitting air therethrough;
   a first and second bonding seam formed to engage said interior and exterior membrane and extending partly therebetween for dividing said first and second membranes into a central enclosure and adjacent first and second lateral enclosures;
   a third and fourth bonding seam formed to engage said exterior membrane to said interior membrane between said first and second bonding seams;
   sealing means formed between said first and second membranes for selectively closing off an air passage to each of said first and second lateral enclosures;
   securing means fixed to said exterior membrane for selectively engaging said first and second enclosure to each other, a strap secured transversely to said exterior membrane for applying manipulative forces thereto; and
   closing means for securing a first end of said strap to a second end of said strap.

2. Apparatus according to claim 1 wherein:
   said exterior and interior membranes each comprise polymeric sheet structures and said exterior membrane is substantially thicker than said interior membrane.

* * * * *